(12) United States Patent
Lu et al.

(10) Patent No.: US 12,128,244 B2
(45) Date of Patent: *Oct. 29, 2024

(54) WEARABLE CARDIOVERTER DEFIBRILLATOR (WCD) SYSTEM WITH ACTIVE ECG CABLE SHIELDING

(71) Applicant: WEST AFFUM HOLDINGS DAC, Dublin (IE)

(72) Inventors: Zhong Qun Lu, Everett, WA (US); Douglas K. Medema, Everett, WA (US); Kenneth F. Cowan, Kirkland, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 271 days.

This patent is subject to a terminal disclaimer.

(21) Appl. No.: 17/540,217

(22) Filed: Dec. 1, 2021

(65) Prior Publication Data

US 2022/0088400 A1 Mar. 24, 2022

Related U.S. Application Data

(63) Continuation of application No. 16/812,306, filed on Mar. 7, 2020, now Pat. No. 11,191,971.

(Continued)

(51) Int. Cl.
*A61N 1/04* (2006.01)
*A61N 1/37* (2006.01)
*A61N 1/39* (2006.01)

(52) U.S. Cl.
CPC ........... *A61N 1/3904* (2017.08); *A61N 1/046* (2013.01); *A61N 1/0484* (2013.01); *A61N 1/3704* (2013.01); *A61N 1/3968* (2013.01)

(58) Field of Classification Search
CPC .... A61N 1/046; A61N 1/0484; A61N 1/3704; A61N 1/3904; A61N 1/3968
See application file for complete search history.

(56) References Cited

U.S. PATENT DOCUMENTS

| | | | |
|---|---|---|---|
| 3,724,455 | A | 4/1973 | Unger |
| 4,583,524 | A | 4/1986 | Hutchins |

(Continued)

FOREIGN PATENT DOCUMENTS

| | | |
|---|---|---|
| EP | 3380189 B1 | 10/2018 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Brian T Gedeon
(74) *Attorney, Agent, or Firm* — Polsinelli PC

(57) ABSTRACT

Embodiments of a wearable cardioverter defibrillator (WCD) system are configured to monitor a patient's ECG for shockable arrhythmias and deliver a shock to the patient in response to such a detection. To monitor the patient's ECG with reduced signal noise to improve the system's performance, the system includes a cable assembly having: a signal line; an inner shield and an outer shield; an ECG electrode electrically connected to the signal line of the cable assembly; and an amplifier having first and second input nodes respectively connected to the signal line and the outer shield of the cable assembly. The amplifier's output node is electrically connected to the inner shield of the cable assembly to reduce the reactive load seen by the patient's (Continued)

heart in driving the ECG sensing circuitry, which reduces the noise on the ECG signal outputted by the amplifier.

23 Claims, 6 Drawing Sheets

Related U.S. Application Data

(60) Provisional application No. 62/815,272, filed on Mar. 7, 2019.

(56) References Cited

U.S. PATENT DOCUMENTS

| | | | |
|---|---|---|---|
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Born et al. |
| 5,353,793 | A | 10/1994 | Born |
| RE34,800 | E | 11/1994 | Hutchins |
| 5,392,784 | A | 2/1995 | Gudaitis |
| 5,394,892 | A | 3/1995 | Kenny |
| 5,405,362 | A | 4/1995 | Kramer et al. |
| 5,474,574 | A | 12/1995 | Payne et al. |
| 5,618,208 | A | 4/1997 | Crouse et al. |
| 5,662,690 | A | 9/1997 | Cole et al. |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder |
| 6,427,083 | B1 | 7/2002 | Owen et al. |
| 6,437,083 | B1 | 7/2002 | Owen et al. |
| 6,529,875 | B1 | 3/2003 | Nakajima |
| 6,546,285 | B1 | 4/2003 | Owen et al. |
| 6,671,545 | B1 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,559,902 | B2 | 7/2009 | Ting et al. |
| 7,865,238 | B2 | 1/2011 | Brink |
| 7,870,761 | B2 | 1/2011 | Valentine et al. |
| 7,974,689 | B2 | 7/2011 | Volpe et al. |
| 8,135,462 | B2 | 3/2012 | Owen et al. |
| 8,140,154 | B2 | 3/2012 | Donnelly et al. |
| 8,369,944 | B2 | 2/2013 | Macho et al. |
| 8,548,557 | B2 | 10/2013 | Garstka et al. |
| 8,615,295 | B2 | 12/2013 | Savage et al. |
| 8,644,925 | B2 | 2/2014 | Volpe et al. |
| 8,676,313 | B2 | 3/2014 | Volpe et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,089,685 | B2 | 7/2015 | Sullivan et al. |
| 9,131,901 | B2 | 9/2015 | Volpe et al. |
| 9,132,267 | B2 | 9/2015 | Kaib |
| 9,408,548 | B2 | 8/2016 | Volpe et al. |
| 9,454,219 | B2 | 9/2016 | Volpe et al. |
| 9,592,403 | B2 | 3/2017 | Sullivan |
| 9,878,171 | B2 | 1/2018 | Kaib |
| 10,632,302 | B2 | 4/2020 | Crone et al. |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2006/0173499 | A1 | 8/2006 | Hampton et al. |
| 2006/0178706 | A1 | 8/2006 | Lisogurski et al. |
| 2008/0312709 | A1 | 12/2008 | Volpe et al. |
| 2009/0005827 | A1 | 1/2009 | Weintraub et al. |
| 2010/0007413 | A1 | 1/2010 | Herleikson |
| 2010/0298899 | A1 | 11/2010 | Donnelly et al. |
| 2011/0022105 | A9 | 1/2011 | Owen et al. |
| 2011/0288604 | A1 | 11/2011 | Kaib et al. |
| 2011/0288605 | A1 | 11/2011 | Kaib et al. |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0085538 | A1 | 4/2013 | Volpe et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0012144 | A1 | 1/2014 | Crone |
| 2014/0025131 | A1 | 1/2014 | Sullivan et al. |
| 2014/0046391 | A1 | 2/2014 | Cowan et al. |
| 2014/0070957 | A1 | 3/2014 | Longinotti-Buitoni et al. |
| 2014/0163663 | A1 | 6/2014 | Poddar et al. |
| 2014/0324112 | A1 | 10/2014 | Macho et al. |
| 2014/0378812 | A1 | 12/2014 | Saroka et al. |
| 2015/0039053 | A1 | 2/2015 | Kaib et al. |
| 2015/0328472 | A1 | 11/2015 | Sullivan et al. |
| 2016/0004831 | A1 | 1/2016 | Carlson et al. |
| 2016/0082277 | A1 | 3/2016 | Foshee, Jr. et al. |
| 2017/0157416 | A1 | 6/2017 | Medema et al. |
| 2019/0159696 | A1 | 5/2019 | Meeker et al. |
| 2020/0046962 | A1 | 2/2020 | Lu et al. |

OTHER PUBLICATIONS

LifeCor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

SAMPLE COMPONENTS OF WEARABLE CARDIOVERTER DEFIBRILLATOR (WCD) SYSTEM

SAMPLE COMPONENTS OF EXTERNAL DEFIBRILLATOR

COMPONENTS OF SAMPLE WCD SYSTEM

MULTIPLE ELECTRODES FOR SENSING ECG SIGNALS ALONG DIFFERENT VECTORS

WEARABLE CARDIOVERTER DEFIBRILLATOR (WCD) SYSTEM WITH ACTIVE ECG CABLE SHIELDING

CROSS REFERENCE TO RELATED PATENT APPLICATIONS

This patent application is a continuation application of U.S. patent application Ser. No. 16/812,306 filed Mar. 7, 2020, issued as U.S. Pat. No. 11,191,971, which claims benefit of priority from U.S. Provisional Patent Application No. 62/815,272 filed Mar. 7, 2019, and each is incorporated herein by reference in their entirety for all purposes.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and thus save the patient's life.

All subject matter discussed in this Background section of this document is not necessarily prior art and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventor(s). This approach in and of itself may also be inventive.

BRIEF SUMMARY

The present disclosure describes instances and examples of cardiac monitoring systems (e.g., WCD systems), devices, systems, storage media that may store programs, and methods.

In embodiments, a cardiac monitoring system includes a support structure for wearing by an ambulatory patient. When worn, the support structure maintains electrodes on the patient's body to sense the patient's ECG signal(s). In some embodiments, active ECG cable shielding is used to transmit ECG signals from the electrodes, which can be used to determine whether the patient has an arrhythmia. In some embodiments, the shielding includes an outer shield that is electrically connected to ground or Wilson Central Terminal and an inner shield that is actively driven by an amplifier circuit used to amplify the received ECG signal.

DETAILED DESCRIPTION

A wearable cardioverter defibrillator (WCD) system according to embodiments may protect an ambulatory patient by electrically restarting their heart if needed. Such a WCD system may have a number of components. These components can be provided separately as modules that can be interconnected, or can be combined with other components, and so on.

Figure 1:
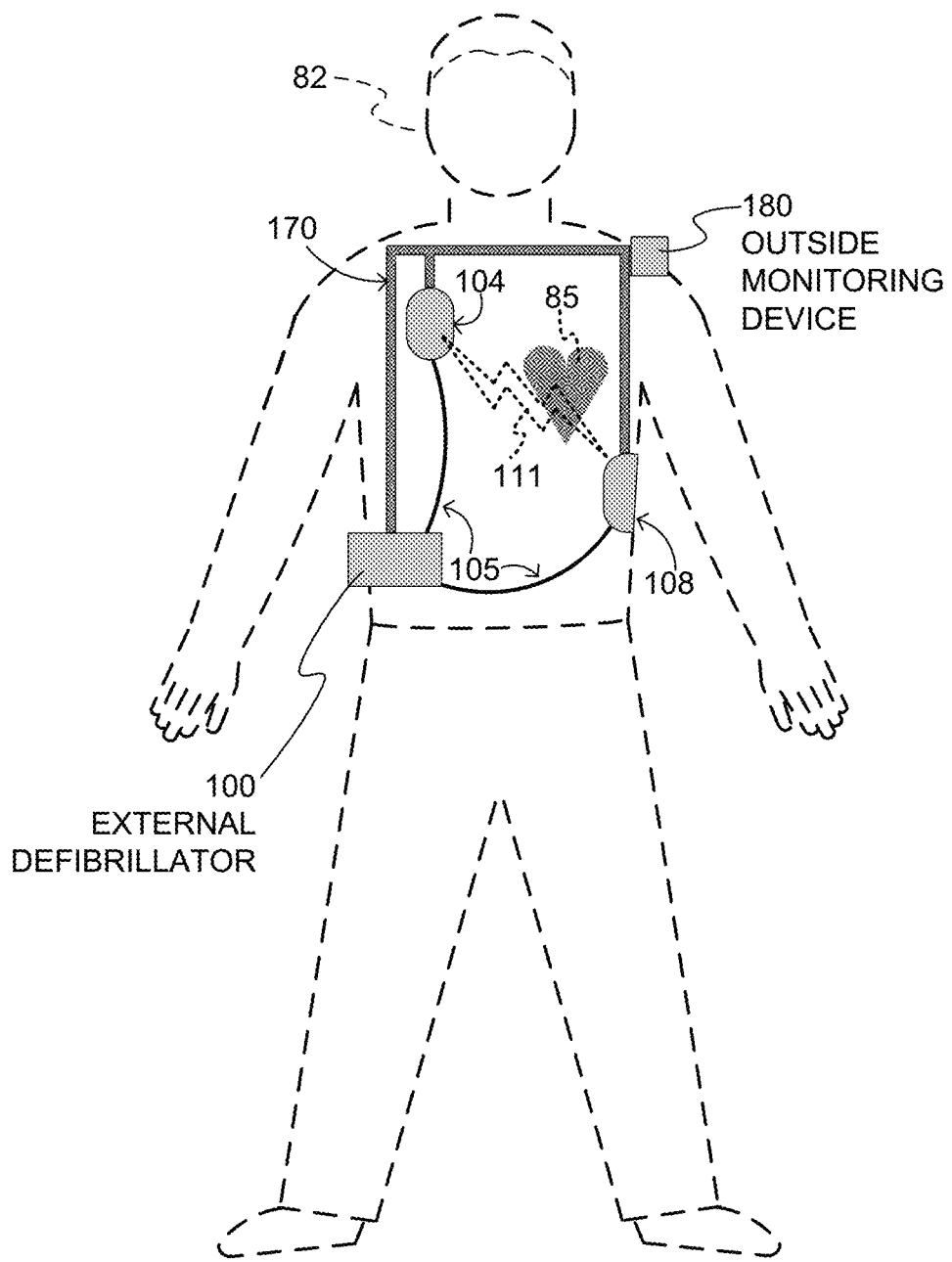
FIG. 1 is a diagram of components of a sample wearable cardioverter defibrillator (WCD) system, made according to embodiments.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as patient physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
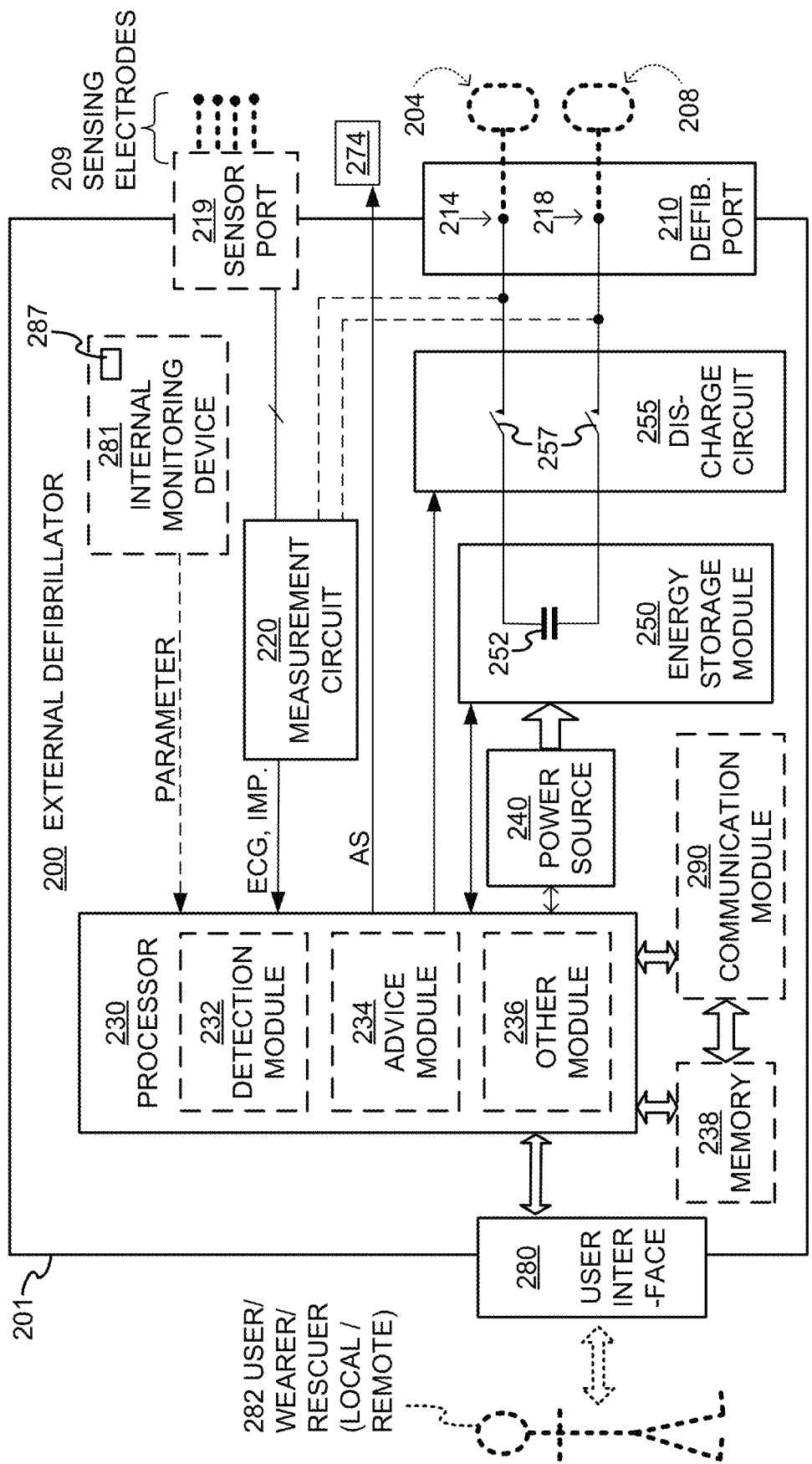
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as US 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in U.S. Published Patent App. Pub. No. 20140043149A1 entitled "MOBILE COMMUNICATION DEVICE & APP FOR WEARABLE DEFIBRILLATOR SYSTEM". This data can be analyzed directly by the patient's physician and can also be analyzed automatically by algorithms designed to detect a developing illness and then notify medical personnel via text, email, phone, etc. Module 290 may also include such interconnected subcomponents as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components.

Figure 3:
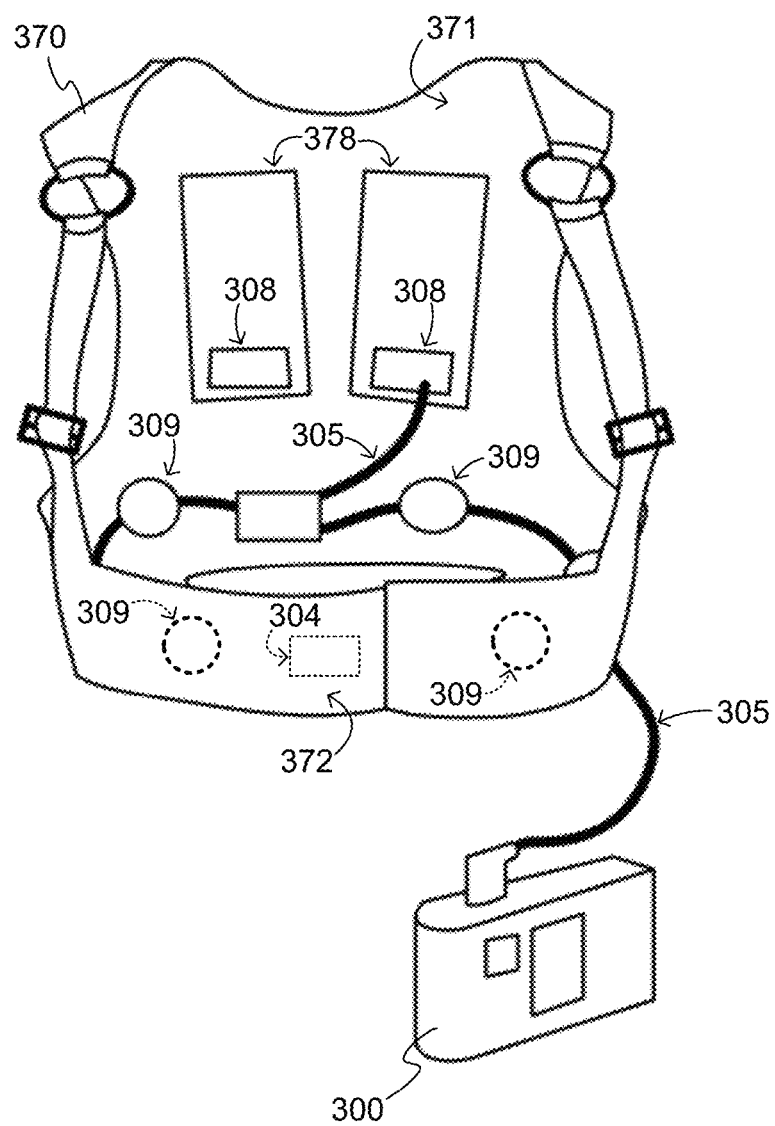
FIG. 3 is a diagram of sample embodiments of components of a WCD system.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. Indeed, back defibrillation electrodes 308 are maintained in pockets 378. Of course, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 4:
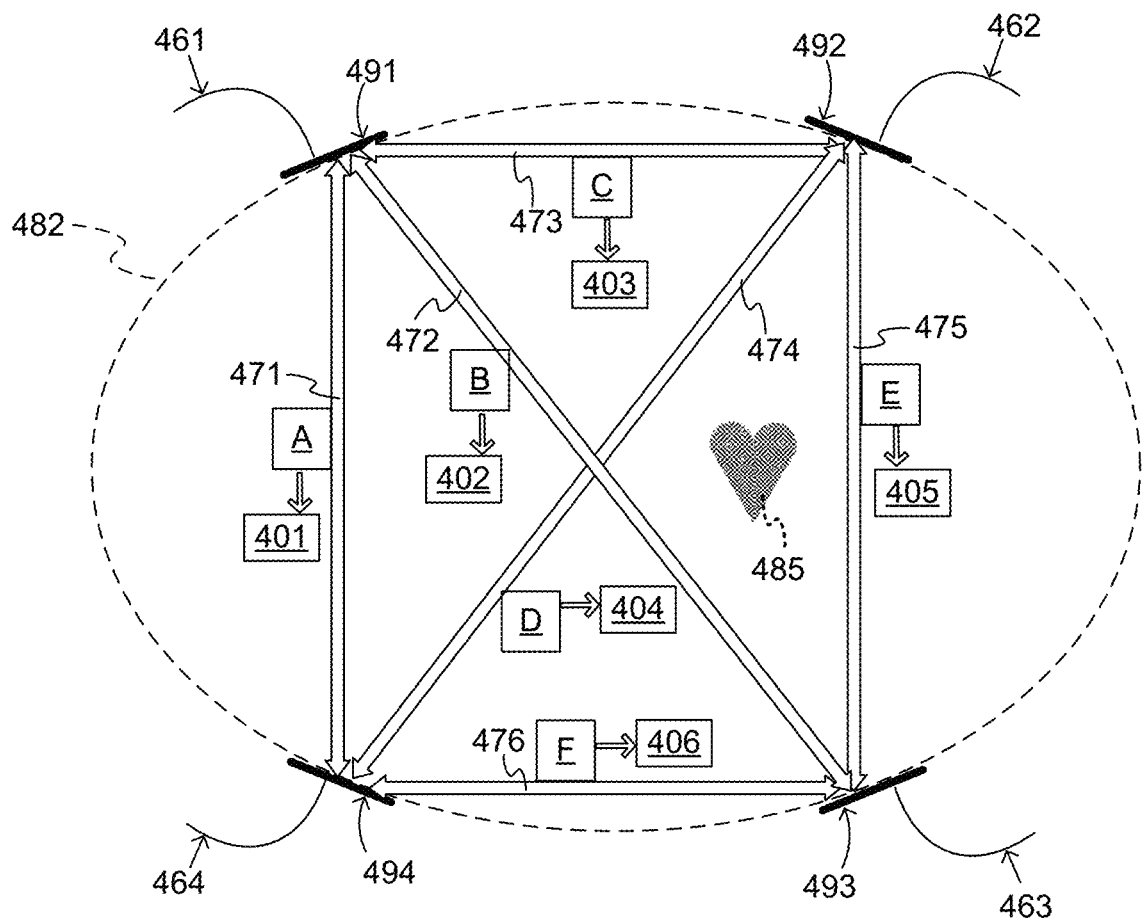
FIG. 4 is a conceptual diagram illustrating how multiple electrodes of a WCD system may be used for sensing ECG signals along different vectors according to embodiments.

FIG. 4 is a conceptual diagram for illustrating how multiple electrodes of a WCD system may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either. Further, some embodiments average value of the voltages of all four electrodes electronically and then determine the voltage of each electrode relative to the average value. Conceptually this average value is the signal at some point in space in between the 4 electrodes. It continuously changes its virtual position based on the voltages of the 4 electrodes. In some embodiments, this virtual point is referred to herein as the M Central Terminal (MCT). Relative to the MCT, there are four resulting vectors: E1C=E1−CM, E2C=E2−CM, E3C=E3−CM and E4C=E4−CM, where CM is the average voltage value. In embodiments, the vectors are formed in software by selecting a pair of these signals and subtracting one from the other. So for example, E1C−E2C=(E1−CM)−(E2−CM) =E1−E2+(CM−CM)=E1−E2=E12. Although six vectors are described in FIG. 4, in other embodiments a different number of vectors may be vectors may be used depending on the number of ECG electrodes used in the system and the desired number of vectors (up to the number of vectors than can be derived from the number of electrodes).

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "WEARABLE CARDIOVERTER DEFIBRILLATOR COMPONENTS MAKING AGGREGATE SHOCK/NO SHOCK DETERMINATION FROM TWO OR MORE ECG SIGNALS", which is incorporated herein by reference.

Figure 5:
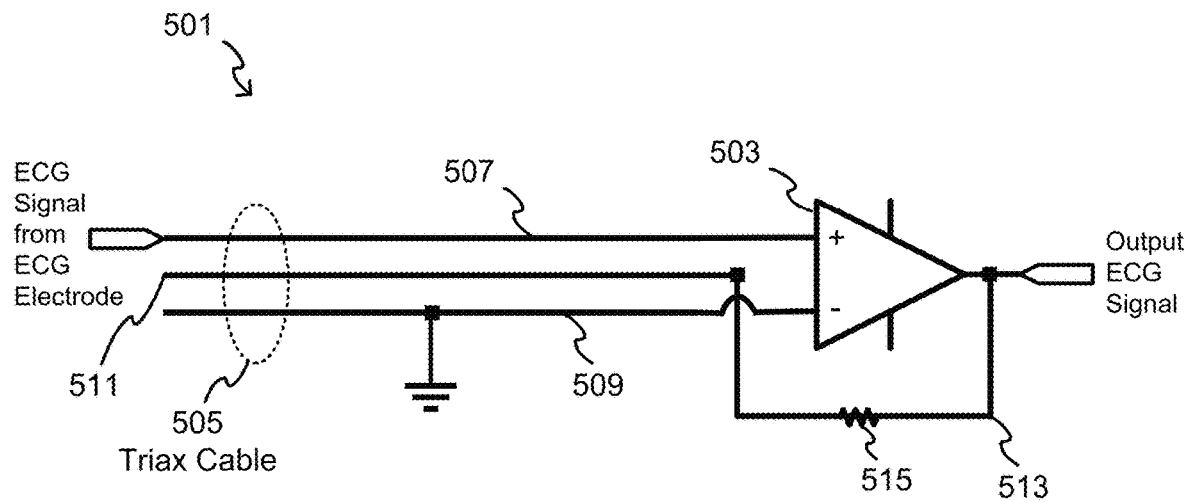
FIG. 5 is a diagram illustrating an interconnect circuit for an ECG sensor, according to embodiments.

FIG. 5 shows an interconnect circuit 501 for an ECG sensor, according to other embodiments. For example, interconnect circuit 501 can be used to propagate sensed signals from one of sensing electrodes 209 FIG. 2, sensing electrodes 309 (FIG. 3), or ECG sensing electrodes 491-493 (FIG. 4). In embodiments, interconnect circuit 501 includes an amplifier 503 connected to one end of a triaxial cable 505, with the other end of the triaxial cable 505 coupled to receive an ECG signal from an ECG electrode (not shown). In some embodiments, amplifier 503 is implemented using an LT1007A operational amplifier or similar device, which are commercially available from several companies such as Analog Devices and Texas Instruments, for example.

In embodiments, triaxial cable 505 includes a signal line 507 and an outer shield 509 respectively connected to the positive and negative input nodes of amplifier 503. Outer shield 509 is connected to a ground terminal, and for embodiments in which the system (e.g., a defibrillator such as defibrillator 200 of FIG. 2) has an isolated ground, outer shield 509 can be electrically connected to an isolated ground terminal. Triaxial cable 505 also includes an inner shield 511, which is connected to the output node of amplifier 503 via an interconnect 513 and a resistor 515. In some embodiments, resistor 515 has a nominal value of 100Ω, but can range from 10Ω to 1MΩ in other embodiments. This relatively low value of resistor 515 helps to ensure the stability of the circuit while keeping the gain close to but slightly less than unity. Further, while a triaxial cable is described, in other embodiments other types of conductive structures having an inner shield and an outer shield arranged about a signal line can be used.

Interconnect circuit 501 may be advantageously used in systems (e.g., the WCD system of FIG. 1) that acquire and interpret the patient's ECG to determine if and when a resuscitation shock needs to be delivered. At the same time, the systems are being used in environments which can make it difficult to acquire ECG signals with sufficient integrity to make the correct interpretation possible. Embodiments of interconnect circuit 501 can improve ECG acquisition in these environments by using inner shield 511 in the cabling to the ECG electrode. In embodiments, inner shield 511 can be electrically driven by circuitry in the ECG preamp (e.g., amplifier 503), so as to lessen the impact of the high impedance electrode-to-skin contacts that are usually present in WCDs and in wearable ECG monitors, especially when using dry electrodes.

WCDs and wearable ECG monitoring systems have an ECG sensing system that must contact the patient's skin for a relatively long time (e.g., up to a month or longer). Long-term wear of adhesive electrodes can have a negative impact on the patient's skin. Using Dry ECG sensing electrodes has much less negative impact on the patient's skin, however, electrode-skin interface may have a much higher impedance than would be found in a typical ECG monitoring system using adhesive electrodes.

The ECG sensing system in effect monitors a small voltage source (the heart) that is connected to an input amplifier through the ECG electrode impedance and a wire or interconnect. This whole circuit can have a high impedance, which can result in the wire picking up noise from sources around the patient.

To combat this external noise sensitivity, in some embodiments the interconnect may include with an outer shield which is connected to a system ground, thus forming a structure similar to a coaxial cable. This shield may totally enclose the signal carrying wire using, for example a braided shield or a wrapped ribbon.

The coaxial cable structure presents a distributed capacitance between the signal-carrying wire and the shield around it, which must be driven by the voltage source (i.e., the heart) through the high impedance of the electrode-skin interface. However, through detailed analysis and investigation, the applicants have appreciated a standard coaxial type structure can have disadvantages when used in WCDs or in wearable ECG monitors, such as:

a. The signal is attenuated by the RC filter formed by the electrode-skin impedance and the capacitance of the cable.
b. The "load" seen by each electrode depends on the length of cable between it and the monitor's amplifier. A WCD or a wearable ECG monitor may employ different lengths of cable to each electrode, so as to minimize the amount of loose cable. This can result in each electrode potentially "seeing" a different load, which can result in slightly different gain. When large common mode signals are present, this difference in gain among the ECG signals from the different electrodes may results in a differential signal being detected across different electrodes lowering the Common Mode Rejection which in turn results in more noise present in the ECG.

These effects can result in a degraded ECG signal being presented to the analysis component of a WCD or a wearable ECG monitor; such ECG signals can potentially negatively affect the ability of the analysis component to provide a correct interpretation of the ECG signals. In WCD applications, any impairment of ECG signal quality has the potential to result in an incorrect analysis, resulting either in preventing a needed shock or in shocking the patient incorrectly.

Embodiments of interconnect circuit 501 can mitigate the second of the detrimental effects described above. Outer shield 509 is similar to the shield described above which totally encloses signal line 507, while inner shield 511 is a third conductor with insulation between it and both the signal line 507 and outer shield 509. In some embodiments, inner shield 511 can be a braid or wrapped ribbon. Further, in some embodiments inner shield 511 can totally enclose the signal line 507 and is in turn totally enclosed by outer shield 509. Inner shield 511 is driven by amplifier 503 with essentially the same signal produced by the heart that is received on signal line 507 with a very slight delay. Note that there is still distributed capacitance between inner shield 511 and outer shield 509, but amplifier 503 driving inner shield 511 can easily overcome this since it has a low output impedance and there is only a small impedance (resistor 515) between amplifier 503 and inner shield 511.

Because of the structure of triaxial cable 505, there is a distributed capacitance between signal line 507 and inner shield 511. The result of driving inner shield 511 is to significantly reduce the voltage difference across the distributed capacitance that must be driven by the voltage source (i.e., the heart). Since the voltage of inner shield 511 is substantially the same as that of signal line 507, there is substantially no voltage difference across the distributed capacitance and thus the distributed capacitance does not need to be charged and discharged by the heart. This effectively greatly reduces the load "seen" by the heart, while still allowing the electric field shielding provided by the outer shield. Since the load is reduced by such a large factor, the fact that the electrode impedance is large or differs between the electrodes no longer affects the Common Mode Rejection thus improving the overall signal quality.

Figure 6:
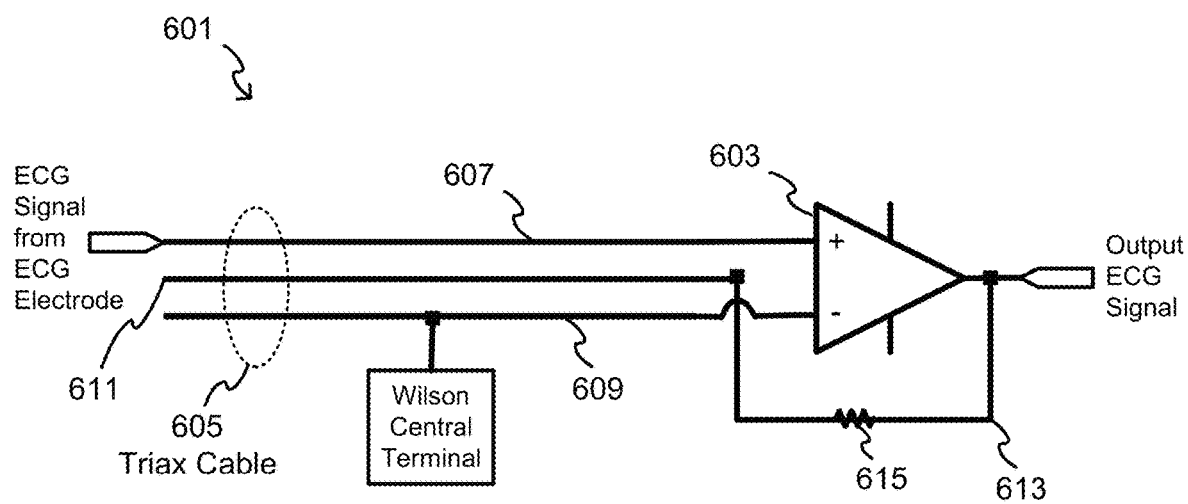
FIG. 6 is a diagram illustrating an interconnect circuit for an ECG sensor, according to other embodiments.

FIG. 6 is a diagram illustrating an interconnect circuit 601 for an ECG sensor, according to other embodiments. Interconnect circuit 601 is substantially similar to interconnect circuit 501 (FIG. 5), except the outer shield is connected to a Wilson Central Terminal instead of a ground or isolated ground terminal. Embodiments of interconnect circuit 601 is described in more detail below.

In embodiments, interconnect circuit 601 includes an amplifier 603 connected to one end of a triaxial cable 605, with the other end of the triaxial cable 605 coupled to receive an ECG signal from an ECG electrode (not shown). More specifically in these embodiments, triaxial cable 605 includes a signal line 607 and an outer shield 609 respectively connected to the positive and negative input nodes of amplifier 603. Outer shield 609 is connected to a Wilson Central Terminal. In some embodiments, amplifier 603 is implemented using an LT1007A operational amplifier or similar device, which are commercially available from several companies such as Analog Devices and Texas Instruments, for example.

Triaxial cable 605 also includes an inner shield 611, which is connected to the output node of amplifier 603 via an interconnect 613 and a resistor 615. In some embodiments, resistor 615 has a nominal value of 100Ω, but can range from 10Ω to 1MΩ in other embodiments. This relatively low value of resistor 615 helps to ensure the stability of the circuit while keeping the gain close to but slightly less than unity. Interconnect circuit 601 operates in a substantially similar manner to interconnect circuit 501 (FIG. 5), but a short summary is provided below.

Inner shield 611 is driven by amplifier 603 with essentially the same signal produced by the heart that is received on signal line 607 with a very slight delay. Amplifier 603 driving inner shield 611 can easily overcome the distributed capacitor between the inner and outer shields because of its low output impedance and the small impedance (resistor 615) between amplifier 603 and inner shield 611. Amplifier 603 driving inner shield 611 can significantly reduce the voltage difference across the distributed capacitance that must be driven by the voltage source (i.e., the heart). Since the voltage of inner shield 611 is substantially the same as that of signal line 607, there is substantially no voltage difference across the distributed capacitance and thus the distributed capacitance does not need to be charged and discharged by the heart. This effectively greatly reduces the load "seen" by the heart, while still allowing the electric field shielding provided by the outer shield. Since the load is reduced by such a large factor, the fact that the electrode impedance is large or differs between the electrodes no longer affects the Common Mode Rejection thus improving the overall signal quality.

Figure 7:
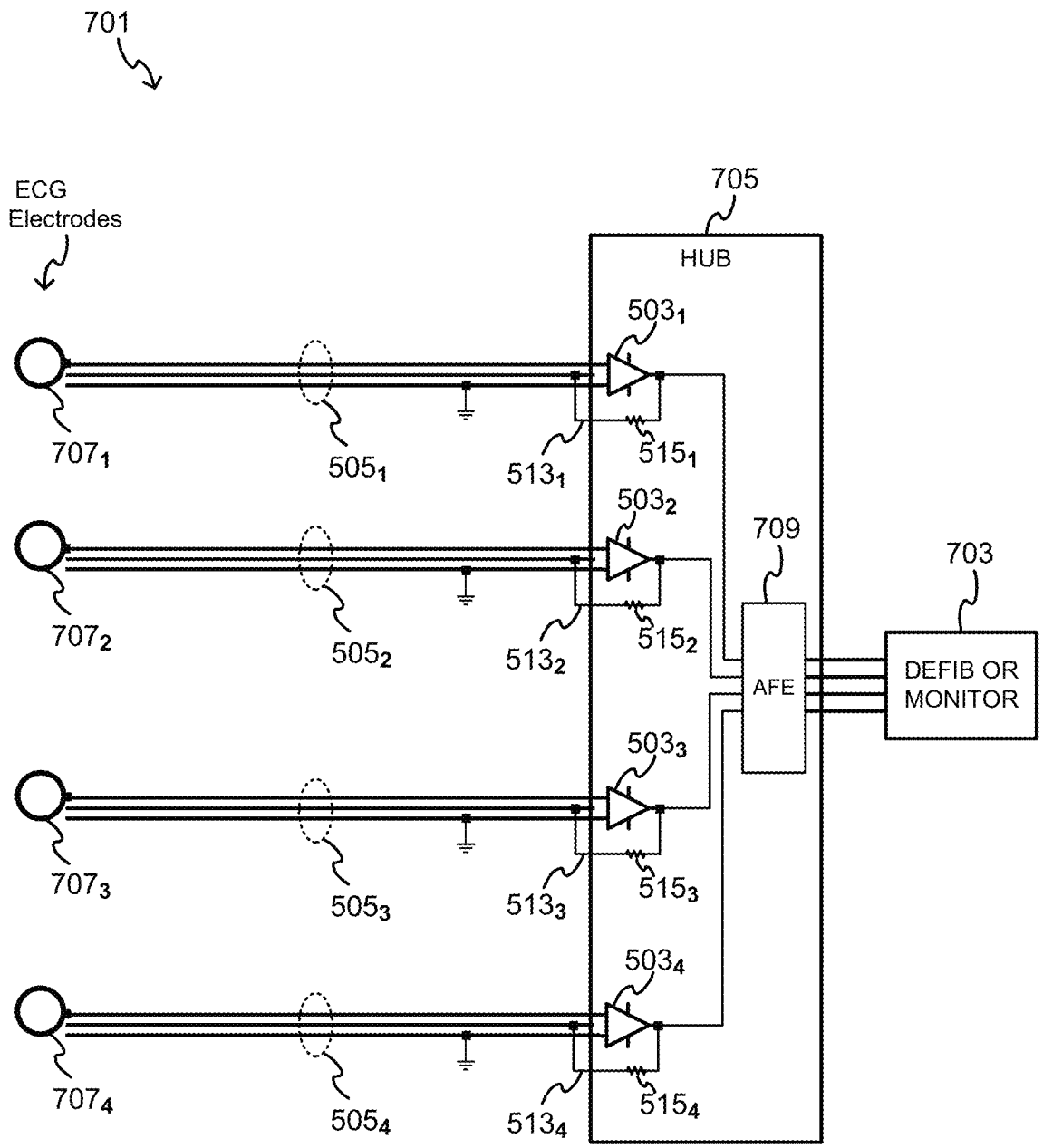
FIG. 7 is a diagram illustrating is a diagram illustrating a multi-sensor ECG interconnect circuit, according to embodiments.

FIG. 7 is a diagram illustrating a multi-sensor ECG interconnect system 701, according to embodiments. This example embodiment can be advantageously used in a WCD (e.g., the WCD illustrated in FIG. 4) or a wearable ECG monitoring system having four ECG sensing electrodes.

In embodiments, interconnect system 701 includes a wearable ECG analysis device 703, such as included in an external defibrillator or external ECG monitor. In embodiments, external ECG analysis device 703 is connected receive ECG signal data via a hub 705 and ECG electrodes 707$_1$-707$_4$. In this example embodiment of FIG. 7, ECG electrodes 707$_1$-707$_4$ are connected to hub 705 via triaxial cables 505$_1$-505$_4$, each of which are substantially similar to triaxial cable 505 (FIG. 5). Hub 705 includes amplifiers 503$_1$-503$_4$ and resistors 515$_1$-515$_4$, each of which are connected to the inner and outer shields of corresponding triaxial cables 505$_1$-505$_4$ in a substantially similar manner as described above for interconnect circuit 501 (FIG. 5). Thus, each of the ECG interconnect circuits corresponding to ECG sensing electrodes 707$_1$-707$_4$ have the reduced noise sensitivity as described above for interconnect circuit 501 (FIG. 5). While four interconnect circuits are illustrated in FIG. 7, the number interconnect circuits can be different in other embodiments.

In some embodiments, hub 705 also includes an analog front end (AFE) module 709, which can include filters, analog-to-digital converters, amplifiers, etc. for transmitting ECG signal data to external analysis device 703. This transmission between hub 705 and external analysis device 703 can be wired or wireless (Bluetooth, for example), and in some embodiments the transmitted data may be digitized samples of the ECG signals sensed via ECG sensing electrodes 707$_1$-707$_4$.

In other embodiments, the outer shields of triaxial cables 505$_1$-501$_4$ are connected to a Wilson Central Terminal in a substantially similar manner as interconnect circuit 601 (FIG. 6). In other embodiments, instead of 4 ECG sensing electrodes, N ECG electrodes can be used, N being a positive integer greater than two. Such embodiments would have ECG sensing electrodes 701$_1$-701$_N$, triaxial cables 505$_1$-505$_N$, amplifiers 503$_1$-503$_N$ and resistors 515$_1$-515$_N$, interconnected as described above.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A cardiac monitoring system for a patient capable of being ambulatory, the cardiac monitoring system comprising:
    a first cable assembly comprising a signal line, an inner shield, and an outer shield;
    a first ECG electrode electrically connected to the signal line of the first cable assembly;
    an amplifier having:
        a first input node electrically connected to the signal line of the first cable assembly,
        a second input node electrically connected to the outer shield of the first cable assembly, and
        an output node electrically connected to the inner shield of the first cable assembly;
    a support structure configured to be worn by the patient and structured to position the first ECG electrode to contact a body of the patient while the support structure is worn by the patient; and
    one or more processors configured to:
        monitor the patient's heart rhythm, wherein to monitor the patient's heart rhythm comprises the one or more processors being configured to receive at least one ECG signal via the first cable assembly and the first ECG electrode.

2. The cardiac monitoring system of claim 1, wherein the outer shield of the first cable assembly is electrically connected to a ground terminal.

3. The cardiac monitoring system of claim 1, wherein the first cable assembly comprises a triaxial cable.

4. The cardiac monitoring system of claim 1, further comprising a hub coupled to the support structure, wherein the amplifier is disposed in the hub.

5. The cardiac monitoring system of claim 1, further comprising a housing, wherein the one or more processors are disposed in the housing.

6. The cardiac monitoring system of claim 5, further comprising a hub, wherein:
    the amplifier is disposed in the hub; and
    the at least one ECG signal received by the one or more processors is generated from an output signal of the amplifier.

7. The cardiac monitoring system of claim 6, wherein the hub further comprises a module including an analog-to-digital converter having:
    an input node coupled to the output node of the amplifier; and
    an output node coupled to the one or more processors.

8. The cardiac monitoring system of claim 1, further comprising:
    a second cable assembly comprising a signal line, an inner shield, and an outer shield;
    a second ECG electrode electrically coupled to the signal line of the second cable assembly;
    a third cable assembly comprising a signal line, an inner shield, and an outer shield;
    a third ECG electrode electrically coupled to the signal line of the third cable assembly;
    a fourth cable assembly comprising a signal line, an inner shield, and an outer shield; and
    a fourth ECG electrode electrically coupled to the signal line of the fourth cable assembly.

9. The cardiac monitoring system of claim 8, wherein the outer shield of the first, second, third and fourth cable assemblies are electrically connected to a ground terminal.

10. The cardiac monitoring system of claim 9, further comprising an isolated ground terminal, wherein the ground terminal is the isolated ground terminal.

11. The cardiac monitoring system of claim 8, wherein the outer shield of the first, second, third and fourth cable assemblies are electrically connected to a Wilson Central Terminal.

12. A wearable cardiac monitoring system for a patient capable of being ambulatory, the wearable cardiac monitoring system comprising:
    a first cable assembly comprising a signal line, an inner shield, and an outer shield;
    a first ECG electrode electrically connected to the signal line of the first cable assembly;
    an amplifier having:
        a first input node electrically connected to the signal line of the first cable assembly,
        a second input node electrically connected to the outer shield of the first cable assembly, and
        an output node electrically connected to the inner shield of the first cable assembly;
    a support structure configured to be worn by the patient and structured to position the first ECG electrode to contact a body of the patient while the support structure is worn by the patient; and
    one or more processors configured to monitor the patient's heart rhythm, wherein to monitor the patient's heart rhythm comprises the one or more processors being configured to receive at least one ECG signal via the first cable assembly and the first ECG electrode.

13. The wearable cardiac monitoring system of claim 12, wherein the outer shield of the first cable assembly is electrically connected to a ground terminal.

14. The wearable cardiac monitoring system of claim 12, wherein the first cable assembly comprises a triaxial cable.

15. The wearable cardiac monitoring system of claim 12, further comprising a hub coupled to the support structure, wherein the amplifier is disposed in the hub.

16. The wearable cardiac monitoring system of claim 12, further comprising a housing, wherein the one or more processors are disposed in the housing.

17. The wearable cardiac monitoring system of claim 16, further comprising a hub, wherein:
    the amplifier is disposed in the hub; and
    the at least one ECG signal received by the one or more processors is generated from an output signal of the amplifier.

18. The wearable cardiac monitoring system of claim 17, wherein the hub further comprises a module including an analog-to-digital converter having:
- an input node coupled to the output node of the amplifier; and
- an output node coupled to the one or more processors.

19. The wearable cardiac monitoring system of claim 12, further comprising:
- a second cable assembly comprising a signal line, an inner shield, and an outer shield;
- a second ECG electrode electrically coupled to the signal line of the second cable assembly;
- a third cable assembly comprising a signal line, an inner shield, and an outer shield;
- a third ECG electrode electrically coupled to the signal line of the third cable assembly;
- a fourth cable assembly comprising a signal line, an inner shield, and an outer shield; and
- a fourth ECG electrode electrically coupled to the signal line of the fourth cable assembly.

20. The wearable cardiac monitoring system of claim 19, wherein the outer shield of the first, second, third and fourth cable assemblies are electrically connected to a Wilson Central Terminal.

21. The wearable cardiac monitoring system of claim 19, wherein the outer shield of the first, second, third and fourth cable assemblies are electrically connected to a ground terminal.

22. The wearable cardiac monitoring system of claim 21, further comprising an isolated ground terminal, wherein the ground terminal is the isolated ground terminal.

23. A method for use in a cardiac monitoring system capable of being worn by an ambulatory patient, the method comprising:
- positioning, by a support structure of the cardiac monitoring system, a first ECG electrode to contact the skin of the patient while the cardiac monitoring system is being worn by the patient;
- coupling the first ECG electrode to a processor of the cardiac monitoring system using a first cable assembly having at least a signal line, an inner shield, and an outer shield, wherein:
  - a first end of the signal line is electrically connected to the first ECG electrode,
  - a second end of the signal line is electrically connected to a first input node of an amplifier,
  - the outer shield is electrically connected to a second input node of the amplifier and to a ground terminal, and
  - the inner shield is electrically connected to an output node of the amplifier via a resistor; and
- monitoring the patient's heart rhythm, wherein monitoring the patient's heart rhythm comprises:
  - receiving at least one ECG signal via the first cable assembly, the first ECG electrode, and the output node of the amplifier.

* * * * *